United States Patent [19]

Effland et al.

[11] Patent Number: 4,517,195
[45] Date of Patent: May 14, 1985

[54] PYRROLO[1,2-B][1,2,5]TRIAZEPINES AND PHARMACEUTICAL COMPOSITIONS THEREOF

[75] Inventors: Richard C. Effland; Joseph T. Klein, both of Bridgewater; R. Richard L. Hamer, Budd Lake, all of N.J.

[73] Assignee: Hoechst-Roussel Pharmaceuticals Inc., Somerville, N.J.

[21] Appl. No.: 627,329

[22] Filed: Jul. 2, 1984

[51] Int. Cl.³ .............. A61K 31/55; C07D 255/02; C07D 255/04
[52] U.S. Cl. .............. 514/413; 260/239.3 B; 548/557; 548/465; 544/372
[58] Field of Search .............. 260/239.3 B; 424/269

[56] References Cited

U.S. PATENT DOCUMENTS

| | | | |
|---|---|---|---|
| 3,121,081 | 2/1964 | Dickinson | 260/240 |
| 4,022,766 | 5/1977 | Fontanella et al. | 260/239.3 B |
| 4,201,712 | 5/1980 | Weber et al. | 260/239.3 B |
| 4,402,970 | 9/1983 | Mariani et al. | 260/239.3 B |

OTHER PUBLICATIONS

Essassi et al. "J. Het. Chem." vol. 20, pp. 1015–1018 (1983) French along with partial English Translation.
Flitsch et al. "Chem. Ber." vol. 102, pp. 3268–3276 (1967).
Dickinson et al. "J. Org. Chem." vol. 27, No. 7, pp. 2470–2473 (1962).
Fontenella et al. "European J. Med. Chem."–Chimica Therapentica vol. 11, No. 3, pp. 217–220 (1976).

Primary Examiner—Robert T. Bond
Attorney, Agent, or Firm—Tatsuya Ikeda

[57] ABSTRACT

There are described novel pyrrolo[1,2-b][1,2,5]triazepines of the general formula

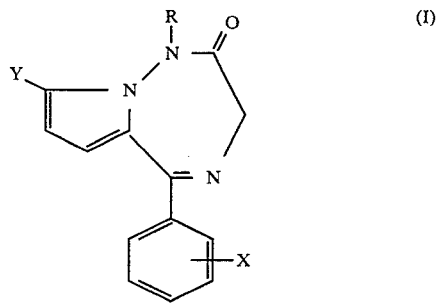

where R is hydrogen, loweralkyl, loweralkylaminoloweralkyl or diloweralkylaminoloweralkyl; X is hydrogen, halogen (fluorine, chlorine, bromine or iodine), trifluoromethyl or nitro; and Y is hydrogen, halogen or loweralkyl. Also described are derivatives of 1-amino-2-benzoylpyrrole having the general formula

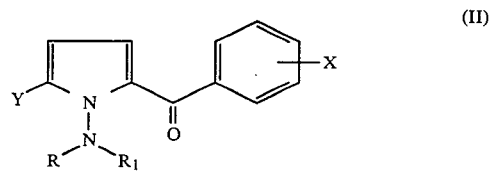

where R, X and Y are as defined above, and $R_1$ is hydrogen,

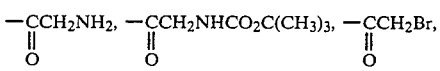

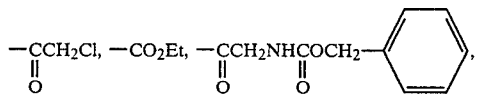

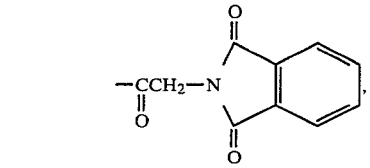

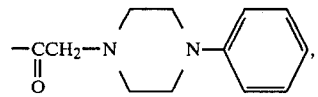

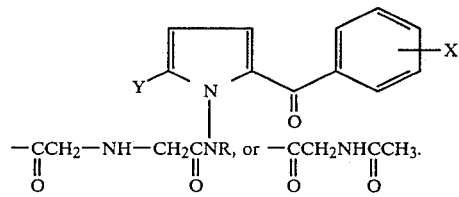

Compounds I and II are useful as analgesic, anxiolytic and/or anticonvulsant agents, and many of Compounds II are useful as intermediates for synthesizing Compounds I.

32 Claims, No Drawings

PYRROLO[1,2-B][1,2,5]TRIAZEPINES AND PHARMACEUTICAL COMPOSITIONS THEREOF

This invention relates to novel pyrrolo[1,2-b][1,2,5]-triazepines of the general formula

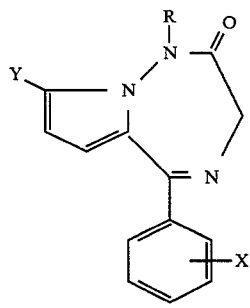
(I)

where R is hydrogen, loweralkyl, loweralkylaminoloweralkyl or diloweralkylaminoloweralkyl; X is hydrogen, halogen (fluorine, chlorine, bromine or iodine) trifluoromethyl or nitro; and Y is hydrogen, halogen or loweralkyl, or a pharmaceutically acceptable acid addition salt thereof. This invention also relates to derivatives of 1-amino-2-benzoylpyrrole having the general formula

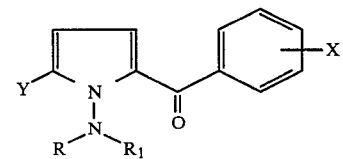
(II)

where R, X and Y are as defined above, and $R_1$ is hydrogen,

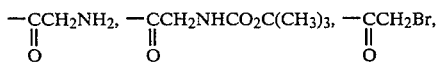

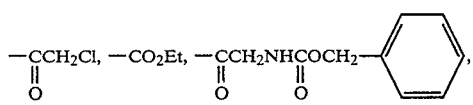

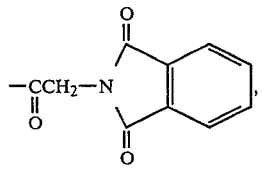

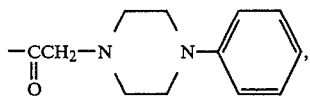

-continued

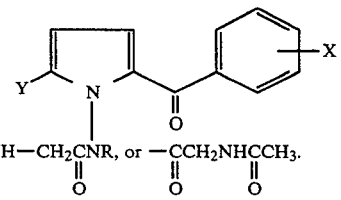

Compounds I and II are useful as analgesic, anxiolytic and/or anticonvulsant agents, and many of Compounds II are useful as intermediates for synthesizing Compounds I.

This invention also relates to novel compounds which are derivatives of 2-benzoyl-1-phthalimidopyrrole having the general formula (III)

where X and Y are as defined above which are useful as intermediates for synthesizing Compounds I and II.

To the best of our knowledge the compounds of the present invention have not been described or suggested.

Throughout the specification and the appended claims, unless otherwise stated or indicated, the term halogen shall mean fluorine, chlorine, bromine or iodine, and the term loweralkyl shall mean an alkyl group of 1-6 carbon atoms.

Compounds of this invention may be prepared by using one or more of the following steps. Unless otherwise stated or indicated, the definitions of the groups R, $R_1$, X and Y are as described above, and the same symbols have the same meanings throughout the descriptions of the reaction steps given below.

STEP A

Compound III may be obtained by reacting a compound of Formula IV with

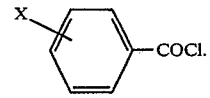

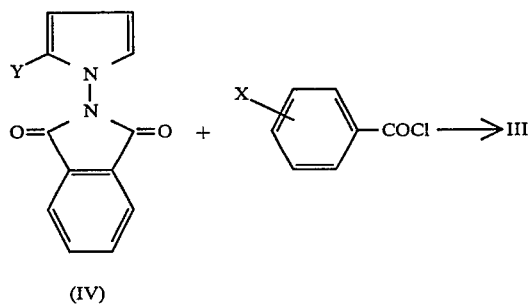

(IV)

Said reaction may be conducted in the presence of zinc chloride in a suitable solvent such as dichloroethane. A typical reaction condition is stirring the reaction mixture at room temperature overnight and additionally at 80° for 1 hour.

Compound IV may be prepared by using the method described in Flitsch et al., Chem. Ber. 1969, Vol. 102, pgs. 3268–3276.

STEP B

Compound IIa may be obtained by hydrolyzing Compound III in a suitable medium such as $H_2O/CH_3NH_2/DMF$ or $H_2O/CH_3NH_2/EtOH$. A typical reaction condition is stirring the reaction mixture at room temperature for several hours.

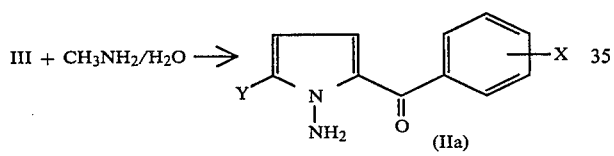

(STEPS C through E relate to the synthesis of Compounds II in which R is hydrogen and $R_1$ is loweralkyl.)

STEP C

Compound V may be obtained by reacting Compound IIa with ethyl chloroformate.

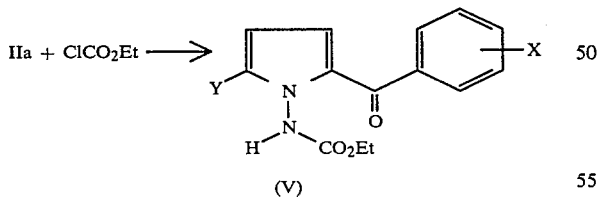

Said reaction is conducted usually in the presence of an acid scavenger such as sodium bicarbonate in a suitable solvent such as dichloromethane. A typical reaction condition is refluxing the reaction mixture for several hours.

STEP D

Compound IV may be obtained by reacting Compound V with a loweralkyl halide of the formula $R_2$-Hal, Hal being iodine, bromine or chlorine, preferably iodine, and $R_2$ being loweralkyl.

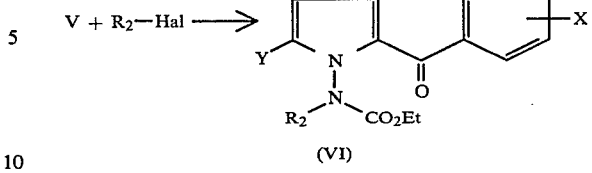

Said reaction is conducted usually in the presence of an acid scavenger such as sodium carbonate in a suitable solvent such as DMF. A typical reaction condition is stirring the reaction mixture at room temperature overnight and additionally at 70°–80° C. for a few hours.

STEP E

Compound VII may be obtained by hydrolyzing Compound VI.

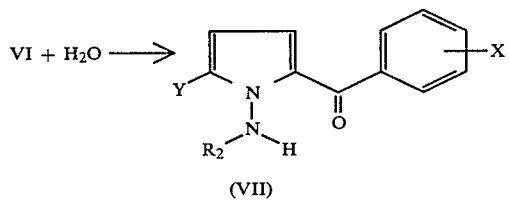

Said reaction is conducted, for instance, in the presence of sodium hydroxide in a suitable solvent such as $H_2O$/ethanol. A typical reaction condition is refluxing the reaction mixture overnight.

(STEPS F and G relate to the synthesis of Compounds II where R is hydrogen and $R_1$ is loweralkylaminoloweralkyl or diloweralkylaminoloweralkyl. In order to simplify the description, STEPS F and G are described with specific reference to the situation where $R_1$ is dimethylaminoethyl.)

STEP F

Compound VIII may be prepared by reacting Compound V with dimethylaminoethyl chloride.

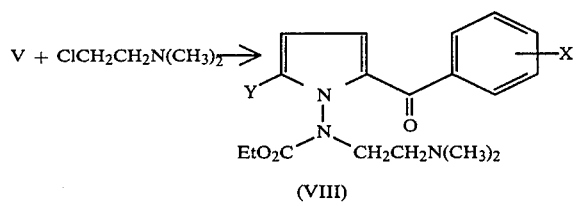

Said reaction is conducted, for instance, in the presence of sodium methoxide in a suitable solvent such as DMF. A typical reaction condition is stirring the reaction mixture at 100° C. for 30 minutes.

STEP G

Compound IX may be obtained by hydrolyzing Compound VIII.

VIII + H₂O ⟶ 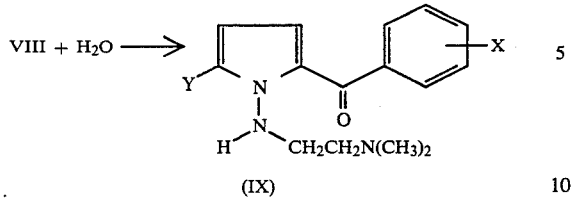
(IX)

Said reaction is conducted, for instance, in the presence of sodium hydroxide in a suitable solvent such as H₂O/ethanol. A typical reaction condition is refluxing the reaction mixture overnight.

Although the description of STEPS F and G above are given with reference to the situation where $R_1$ is dimethylaminoethyl, it will be obvious to the person skilled in the art that the same procedure is generally applicable for preparing Compounds X and XI below where $R_3$ is loweralkylaminoloweralkyl or diloweralkylaminoloweralkyl.

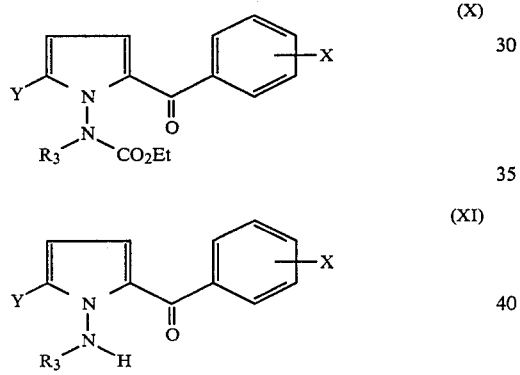

From the foregoing descriptions of STEPS C through G, it will be seen that compounds of the general formula XII can be prepared, where $R_4$ is loweralkyl, loweralkylaminoloweralkyl or diloweralkylaminoloweralkyl.

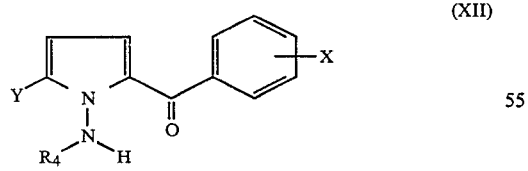

STEP H

Compound XIII may be obtained by reacting Compound XII with N-(tert-butoxycarbonyl)-glycine.

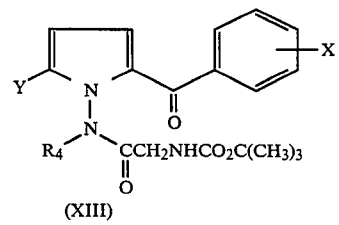
(XIII)

Said reaction is conducted usually in the presence of dicyclohexylcarbodiimide which acts as a dehydrating agent in a suitable solvent such as dichloromethane. A typical reaction condition is stirring the reaction mixture at room temperature for several hours.

STEP I

Compound XIV may be obtained by hydrolyzing Compound XIII.

XIII + H₂O ⟶ 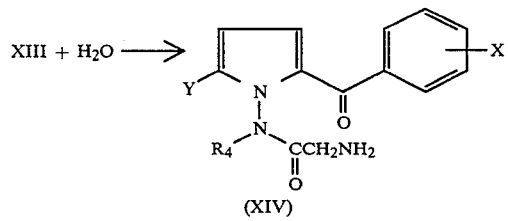
(XIV)

Said reaction is conducted, for instance, by using 48% HBr and a suitable solvent such as ethyl acetate/n-propanol. A typical reaction condition is stirring the reaction mixture at room temperature for several hours.

(As an alternative to adopting STEPS H and I to prepare Compound XIV from Compound XII, the following STEPS J and K may be adopted.)

STEP J

Compound XV may be prepared by reacting Compound XII with bromoacetyl bromide.

XII + BrCCH₂Br ⟶ 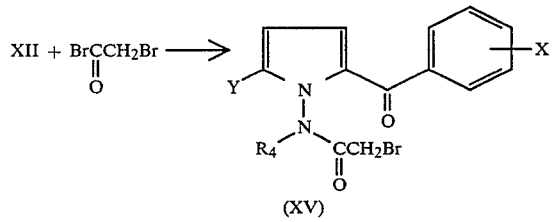
            ‖
            O
(XV)

Said reaction is conducted usually in the presence of an acid scavenger such as sodium bicarbonate in a suitable solvent such as dichloromethane. A typical reaction condition is stirring the reaction mixture at room temperature overnight.

STEP K

Compound XIV may be prepared by first reacting Compound XV with sodium azide and then hydrogenating the resultant azidoacetamido derivative with hydrogen gas in the presence of a suitable catalyst such as platinum.

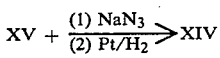

Said reaction with sodium azide may be conducted in a routine manner known to the art. Said hydrogenation reaction may be conducted, for instance, in a suitable solvent such as methanol at a hydrogen gas pressure of 15 psi. A typical hydrogenation condition is shaking the reaction mixture for a few hours at room temperature.

STEP L

Compound Ia may be obtained by cyclizing Compound XIV.

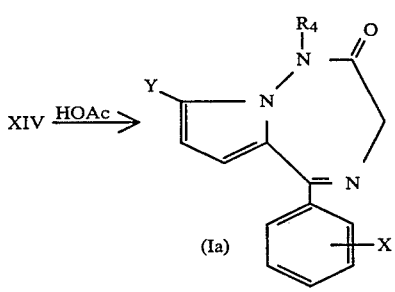

Said reaction is conducted, for instance, in the presence of glacial acetic acid in a suitable solvent such as methanol. A typical reaction condition is refluxing the reaction mixture under nitrogen for several hours.

(Compound Ib corresponding to the situation where R is hydrogen in Formula I may be prepared by using STEPS M and N below.)

STEP M

Compound XVI may be prepared by reacting Compound IIa with bromoacetyl bromide.

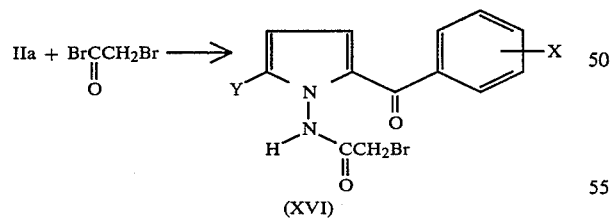

Said reaction is conducted usually in the presence of an acid scavenger such as sodium bicarbonate in a suitable solvent such as dichloromethane. A typical reaction condition is stirring the reaction mixture at room temperature for a few hours.

STEP N

Compound Ib may be prepared by cyclizing Compound XVI.

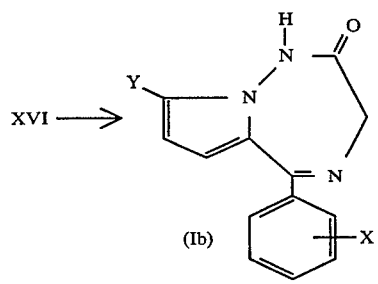

Said reaction may be conducted in the presence of ammonia in a suitable solvent such as methanol. A typical reaction condition is stirring the reaction mixture at room temperature overnight and additionally refluxing it for several hours. Alternatively, said reaction may be conducted in two steps, first reacting Compound XVI with ammonia in a suitable solvent such as methanol at 0° for 10 minutes for instance. After evaporating the volatiles under vacuum, the residue is taken up in a suitable solvent such as isopropanol, and glacial acetic acid is added to the solution. Thereafter, the mixture is refluxed for several hours.

STEP O

As an alternative to the sequence consisting of STEPS M and N to prepare Compound Ib, a method may be used wherein a compound of the formula XVII, XVIII or XIX may first be prepared by using Route O(a), O(b) or O(c) below. Hydrolysis of any of Compound XVII, XVIII or XIX affords Compound XX. Compound XX is then cyclized to afford Compound Ib. The hydrolysis of Compounds XVII and XVIII to afford Compound XX is conducted in substantially the same manner as used for the hydrolysis of Compound XIII to afford Compound XIV which is described in STEP I. The hydrolysis of Compound XIX to afford Compound XX may be conducted in substantially the same manner as used for the hydrolysis of Compound III to afford Compound IIa described in STEP B. The cyclization of XX to afford Ib may be conducted in substantially the same manner as described in STEP L.

ROUTE O(a)

Compound IIa is reacted with N-(tert-butoxycarbonyl)-glycine to afford Compound XVII.

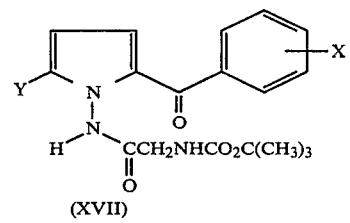

Said reaction is conducted in the presence of dicyclohexylcarbodiimide in a suitable solvent such as dichloromethane. A typical reaction condition is stirring the reaction mixture at room temperature for a few hours and additionally refluxing it for a few hours.

ROUTE O(b)

Compound IIa is reacted with carbobenzyloxyglycine to afford Compound XVIII.

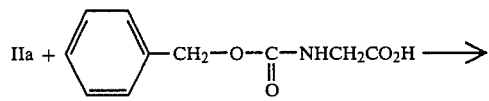

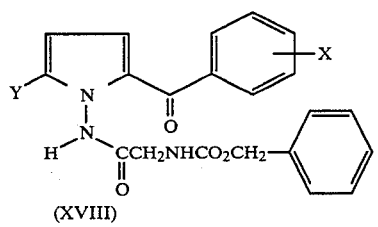
(XVIII)

Said reaction is conducted in the presence of dicyclohexylcarbodiimide in a suitable solvent such as dichloromethane. A typical reaction condition is stirring the reaction mixture at room temperature for a few hours.

ROUTE O(c)

Compound IIa is reacted with N-phthaloyl glycine to afford Compound XIX.

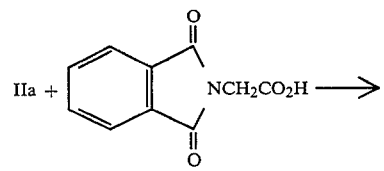

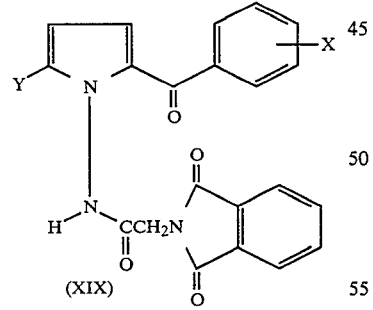
(XIX)

Said reaction is conducted in the presence of dicyclohexylcarbodiimide in a suitable solvent such as dichloromethane. A typical reaction condition is stirring the reaction mixture at room temperature for a few hours and additionally refluxing it for a few hours.

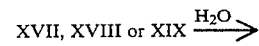
XVII, XVIII or XIX $\xrightarrow{H_2O}$

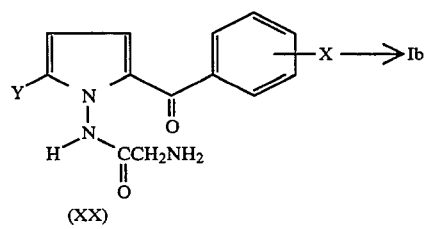
(XX)

The reactions described in Routes O(a), (b) and (c) may also be utilized to obtain compounds XVIIa, XVIIIa and XIXa by reacting Compound XII with N-(tert-butoxycarbonyl)-glycine, carbobenzyloxyglycine and N-phthaloyl glycine, respectively.

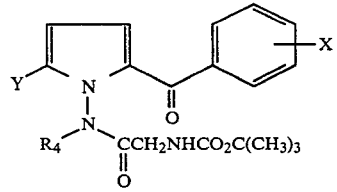
(XVIIa)

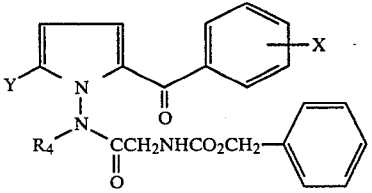
(XVIIIa)

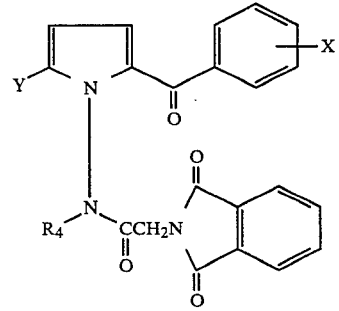
(XIXa)

Any of the Compounds XVIIa, XVIIIa or XIXa may be hydrolyzed to afford compound XIV.

(Compound I where Y is chlorine or bromine may be prepared from Compound Ic and N-chlorosuccinimide or N-bromosuccinimide, respectively, as an alternative to adopting the foregoing steps.)

STEP P

Compound Id may be obtained by reacting Compound Ic with N-chlorosuccinimide.

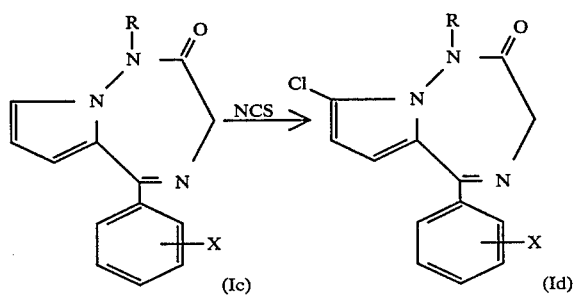

Said reaction is conducted in the presence of a suitable solvent such as dry tetrahydrofuran. A typical reaction condition is refluxing the reaction mixture under nitrogen for several hours.

STEP Q

Compound Ie may be obtained by reacting Compound Ic with N-bromosuccinimide.

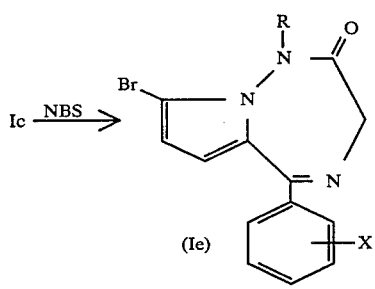

Said reaction is conducted usually in a suitable solvent such as dry tetrahydrofuran. A typical reaction condition is refluxing the reaction mixture for several hours.

STEP R

Compound of Formula XXI may be prepared by reacting Compound XVI with N-phenylpiperazine.

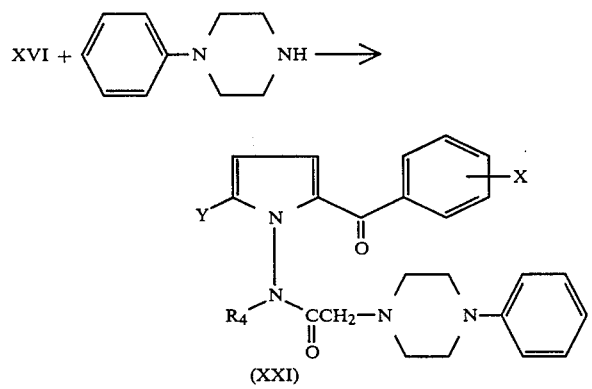

Said reaction is conducted usually in the presence of an acid scavenger such as sodium bicarbonate in a suitable solvent such as dichloromethane. A typical reaction condition is stirring the reaction mixture at 75° for a few hours.

STEP S

A compound of Formula XXII may be prepared by reacting Compound XV with ammonia in a suitable solvent such as methanol and then reacting the resultant product with glacial acetic acid in a suitable solvent such as isopropanol.

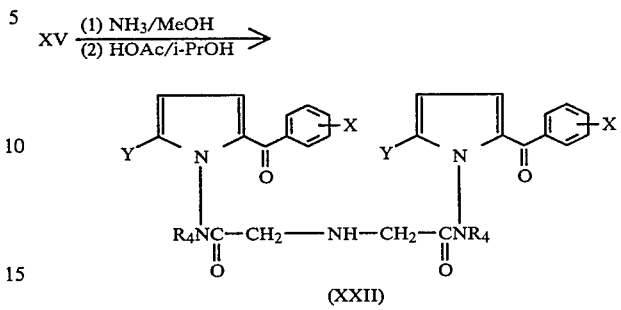

The first step is conducted, for instance, by stirring the reaction mixture at room temperature for a few hours. The second step may be conducted by refluxing the reaction mixture for 5–10 hours.

STEP T

A compound of Formula XXIII may be prepared by reacting Compound XIV with ammonia in a suitable solvent such as methanol, and then reacting the resultant product with glacial acetic acid in a suitable solvent such as isopropanol.

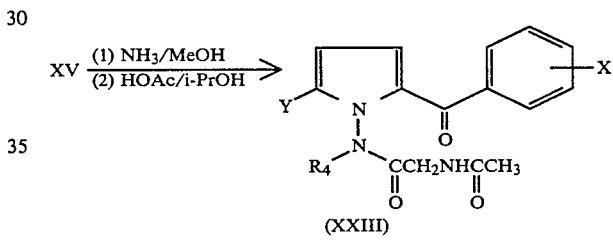

The first step is conducted, for instance, by stirring the reaction mixture for 1 hour and then refluxing it for several hours. The second step may be conducted, for instance, by refluxing the reaction mixture for several days.

All other starting materials shown above are either known compounds or easily prepared by routine methods known to the art from readily available materials.

Compounds I and II of the present invention are useful as analgesic agents due to their ability to alleviate pain in mammals. The activity of the compounds is demonstrated in the 2-phenyl-1,4-benzoquinone-induced writhing test in mice, a standard assay for analgesia, [Proc. Soc. Exptl. Biol. Med., 95, 729 (1957)]. Results of the analgesic activities of some of the compounds of this invention are shown in Table I.

TABLE I

| ANALGESIC ACTIVITY | |
|---|---|
| | PQW (% decrease) (at 20 mg/kg, s.c.) |
| [2-(2-Chlorobenzoyl)-1H—pyrrol-1-yl]-2-[(dimethylamino)ethyl]carbamic acid, ethyl ester hydrobromide | 41% |
| [2-(2-Chlorobenzoyl)-1H—pyrrol-1-yl]-2-(dimethylamino)ethylamine hydrobromide | 72% |
| 1-[N—Methyl-(t-butoxycarbonylamino)-acetamido]-2-(2-chlorobenzoyl)pyrrole | 47% |
| 1-[(t-Butoxycarbonylamino)acetamido]-2-(2-chlorobenzoyl)pyrrole | 49% |
| 1-(N—Methyl-aminoacetamido)-2- | 42% |

TABLE I-continued
ANALGESIC ACTIVITY

| | PQW (% decrease) (at 20 mg/kg, s.c.) |
|---|---|
| (2-chlorobenzoyl)pyrrole hydrobromide | |
| Di-[(2-(2-fluorobenzoyl)-5-methyl-1H—pyrrol-1-yl)-2-acetamido]amine hydrochloride | 68% |
| 1-[(Carbobenzyloxyamino)acetamido]-2-benzoylpyrrole | 50% |
| 1-Aminoacetamido-2-benzoylpyrrole hydrochloride | 23% |
| 1-[(t-Butoxycarbonylamino)acetamido]-2-(2-fluorobenzoyl)pyrrole | 21% |
| 5-(2-Chlorophenyl)-1-methyl-1H—pyrrolo-[1,2-b][1,2,5]triazepin-2(3H)—one | 36% |
| 5-Phenyl-1H—pyrrolo[1,2-b][1,2,5]-triazepin-2(3H)—one | 31% |
| 1-Methyl-5-phenyl-1H—pyrrolo[1,2-b]-[1,2,5]triazepin-2(3H)—one hydrobromide | 26% |
| 5-(2-Fluorophenyl)-1-methyl-1H—pyrrolo-[1,2-b][1,2,5]triazepin-2(3H)—one hydrochloride | 27% |
| 8-Chloro-5-(2-fluorophenyl)-1-methyl-1H—pyrrolo[1,2-b][1,2,5]-triazepin-2(3H)—one hydrochloride | 19% |

Compounds I and II of the present invention are useful as anxiolytic agents. The activity of the compounds is demonstrated in the Geller-conflict paradigm with rats. See Geller, Irving and Seifter, Psychopharmacologia Vol. 1, 482–492 (1962). Male rats are used as test subjects. They are housed individually and food and water are available ad libitum until they are 300 to 400 grams prior to the start of training. Subsequently they are food deprived until their body weight is reduced to approximately 80% of original and it is maintained at this level by a restricted food diet.

The programming and test equipment consists of solid state devices, shockers and cages within sound-attenuated environmental enclosures. The data is recorded on both solid state print-out counters and cumulative recorders. The cages are equipped with a houselight, a single-lever, cue-lights, a liquid dipper, a speaker and a grid-floor connected to a shocker. Sweetened condensed milk delivered by the liquid-dipper serve as the positive reinforcement for all subjects.

The subjects are trained to lever-press for the milk reward in two distinct response-reward sections. In the anxiety or "conflict" segment, signaled by onset of both tone and cue-lights, a dipper of milk is delivered in response to each lever-press (CRF schedule of reinforcement). However lever presses during this period are also accompanied by a 40 m sec pulse of aversive footshock through the grid-floor. This creates a "conflict" between 1) easy access to milk reward and 2) the simultaneous presentation of a painful foot-shock. This "conflict" period is 3 minutes in duration.

During the other segment of this paradigm, the lever presses produces a dipper of milk only at variable intervals of time from 60 to 210 seconds with an average reward of once per 2 minutes (VI-2 min.). No shocks are ever administered during this VI phase of testing which is 15 minutes in duration.

The test procedure consists of four 15 minute (non-shock) VI segments where reinforcement was available on a limited basis. Each VI period is followed by a 3 minute "CRF"-conflict phase when reinforcement is constantly available but always accompanied by an aversive foot-shock. The shock-level is titrated for each subject to reduce the CRF responding to a total of less than 10 lever-presses during the entire test. The rats are tested four days a week. Drugs are administered on the third day and the performance is compared to the previous days control trial. The VI responses are used to evaluate any general debilitating drug effects, while the CRF responses are used to evaluate any "anti-anxiety" effects as indicated by increased responding during the "CRF-conflict" period.

All test compounds are administered by intraperitoneal injection in volumes of 10 cc/kg and the pretreat interval is usually one-half hour.

Compounds I and II of the present invention are useful as anticonvulsant agents. The activity of the compounds is demonstrated in supramaximal electroshock assay. Groups of male mice (18–30 grams) are used. Drugs are prepared using distilled water and if insoluble, a surfactant is added. Control animals receive vehicle. Drugs are routinely administered intraperitoneally. The dosage volume is 10 ml/kg.

The animal's eyes are placed across the output terminals of an A.C. shocker that delivers 206 volts rms for 300 milliseconds. Electrode paste coats the animal's eyes at the point of contact with the terminals.

A compound is considered to give protection if the mouse does not exhibit extensor tonus. Protection is expressed as normalized percent inhibition relative to vehicle control.

$$\text{Normalized \% inhibition} = \frac{\frac{\# Rx \text{ protected}}{\# Rx \text{ tested}} - \frac{\# \text{Control protected}}{\# \text{Control tested}}}{1 - \frac{\# \text{Control protected}}{\# \text{Control tested}}} \times 100$$

A time response is carried out using 6 animals per group. Animals are tested at 30, 60 and 120 minutes postdrug. Additional time periods are tested if indicated by previous tests.

When the peak activity time has been determined, a dose response is initiated, using 10 animals per group at that time period. The $ED_{50}$ and 95% confidence interval are calculated by computerized probit analysis.

Results of the anxiolytic and anticonvulsant activities of some of the compounds of this invention are shown in Table II.

Table II also lists benzodiazepine binding properties of some of the compounds of this invention. This assay is used to determine potential anxiolytic or anticonvulsant activity via direct interaction with benzodiazepine recognition sites in a membrane preparation obtained from rat brain.

Benzodiazepine is a widely prescribed pyschoactive agent. It has various pharmacological properties, including anti-anxiety, anticonvulsant, muscle relaxant and hypnotic effects. The relationships between the pharmacological activities of this compound and the GABA receptor-chloride ionophore complex have been studied in the past. The values of $IC_{50}$ listed in Table II were determined in the following manner. See Squires and Braestrup, "Benzodiazepine Receptors in Rat Brain", Nature, 266, 732–734 (1977).

Reagents

1. Tris Buffer pH 6.9:
   a. 78.1 g of Tris-HCl q.s. to 1 liter
   b. 60.6 g of Tris-base q.s. to 1 liter c. Adjust pH of Tris HCl to 6.9 at 25° C. by adding Tris base to obtain 0.5 M Tris buffer, pH 6.9.
d. Make a 1:10 dilution with distilled H$_2$O to obtain 0.05 M Tris buffer, pH 6.9 test drug is defined as that concentration of the test drug at which said ratio becomes 50% (IC stands for inhibitory concentration).

TABLE II

| ANXIOLYTIC AND ANTICONVULSANT ACTIVITIES | | | |
|---|---|---|---|
|  | Bz Binding (IC$_{50}$,M) | Geller dose/CRF (mg/kg, i.p.) | SES ED$_{50}$ (mg/kg) |
| 5-Phenyl-1H—pyrrolo[1,2-b]-[1,2,5]triazepin-2(3H)—one | 6.73 × 10$^{-6}$ | | |
| 1-Methyl-5-phenyl-1H—pyrrolo-[1,2-b][1,2,5]-triazepin-2(3H)—one hydrobromide | 3.40 × 10$^{-7}$ | 40/22.6 | |
| 5-(2-Fluorophenyl)-1H—pyrrolo-[1,2-b][1,2,5]triazepin-2(3H)—one | 5.86 × 10$^{-7}$ | 40/2.4 | |
| 8-Chloro-5-(2-fluorophenyl)-1-methyl-1H—pyrrolo[1,2-b][1,2,5]-triazepin-2(3H)—one hydrochloride | 6.99 × 10$^{-7}$ | | 36.1 i.p. |
| 5-(2-Chlorophenyl)-1H—pyrrolo-[1,2-b][1,2,5]triazepin-2(3H)—one | 2.04 × 10$^{-7}$ | 60/15 | |
| 5-(2-Chlorophenyl)-1-methyl-1H—pyrrolo[1,2-b][1,2,5]triazepin-2(3H)—one | 2.27 × 10$^{-8}$ | 40/1.4 | 17.9 i.p. |
| 1-(N—Methyl-aminoacetamido)-2-(2-fluorobenzoyl)pyrrole hydrobromide | less than 1.0 × 10$^{-5}$ | 40/11.2 | 8.2 i.p. |
| 5-(2-Fluorophenyl)-1-methyl-1H—pyrrolo[1,2-b][1,2,5]triazepin-2(3H)—one hydrochloride | 6.21 × 10$^{-8}$ | | 43.6 i.p. |

2. 0.32 M sucrose: 21.9 g of sucrose q.s. to 200 ml
3. Radioactive benzodiazepine: this marker compound is made up to a concentration of 80 nM and 50 l of the solution is added to each tube, which yields a final concentration of 2 nM in the assay.
4. Test Compounds: 1 nM stock solution is made up in a suitable vehicle and serially diluted, such that the final concentration in the assay ranges from 10$^{-5}$ to 10$^{-8}$ M.

Tissue Preparation

Male Wistar rats are decapitated and the brain rapidly removed. The cerebral cortices are removed, weighed and homogenized with a homogenizer in 20 volumes of ice-cold 0.32 M sucrose. This homogenate is centrifuged at 1,000 g for 10 minutes, the pellet is discarded and the supernatuant is recentrifuged at 30,000 g for 20 minutes. The resulting membrane pellet is resuspended in 40 volumes of 0.05 M Tris buffer, pH 6.9.

Assay 1 ml 0.05 M Tris buffer, pH 6.9 560 l H$_2$O
70 l 0.5 M Tris buffer, pH 6.9
50 radioactive benzodiazepine solution
20 l vehicle or a solution containing an appropriate concentration of test drug
300 l tissue suspension prepared above A tube containing the first five items listed above is incubated at 0°-4° C. in an ice bath. A 300 l aliquot of the tissue suspension is added to the tube and the sample is then incubated for 20 minutes at 0°-4° C. and thereafter vacuum-filtered using a suitable filter. The filter is immediately rinsed with three 5 ml washes of ice-cold Tris buffer, pH 6.9. The radioactivity of the filter is counted in 10 ml of a counting cocktail. The value of the radioactive counting obtained for a sample containing a test drug is compared to the counting obtained for the sample not containing the test drug and the ratio between the two computed. The IC$_{50}$ value for a given Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspension may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
5-(2-Fluorophenyl)-1H-pyrrolo[1,2-b][1,2,5]triazepin-2(3H)-one;
5-Phenyl-1H-pyrrolo[1,2-b][1,2,5]triazepin-2(3H)-one;
1-Methyl-5-phenyl-1H-pyrrolo[1,2-b][1,2,5]triazepin-2(3H)-one hydrobromide;
5-(2-Chlorophenyl)-1-methyl-1H-pyrrolo[1,2-b][1,2,5]triazepin-2(3H)-one;
5-(2-Chlorophenyl)-1H-pyrrolo[1,2-b][1,2,5]triazepin-2(3H)-one;
8-Chloro-5-(2-fluorophenyl)-1-methyl-1H-pyrrolo[1,2-b][1,2,5]triazepin-2(3H)-one hydrochloride;
5-(2-Fluorophenyl)-1-methyl-1H-pyrrolo[1,2-b][1,2,5]triazepin-2(3H)-one hydrochloride;
5-(2-Fluorophenyl)-8-methyl-1H-pyrrolo[1,2-b][1,2,5]triazepin-2(3H)-one;
1-(N-Methyl-aminoacetamido)-2-benzoylpyrrole fumarate;
1-(N-Methyl-aminoacetamido)-2-(2-chlorobenzoyl)pyrrole hydrobromide;
1-(N-Methyl-aminoacetamido)-2-(2-fluorobenzoyl)pyrrole hydrobromide;
1-[N-Methyl-(t-butoxycarbonylamino)acetamido]-2-(2-chlorobenzoyl)-pyrrole;
1-[(t-Butoxycarbonylamino)acetamido]-2-(2-chlorobenzoyl)pyrrole;
1-[N-Methyl-(t-butoxycarbonylamino)acetamido]-2-(2-fluorobenzoyl)-pyrrole;
1-[(t-Butoxycarbonylamino)acetamido]-2-(2-fluorobenzoyl)pyrrole;
1-Bromoacetamido-2-(2-fluorobenzoyl)pyrrole;
1-Bromoacetamido-2-benzoylpyrrole;
1-(N-Methyl-bromoacetamido)-2-benzoylpyrrole;
1-Chloroacetamido-2-(2-fluorobenzoyl)pyrrole;
1-Bromoacetamido-2-(2-fluorobenzoyl)-5-methylpyrrole;
1-(N-Methyl-bromoacetamido)-2-(2-chlorobenzoyl)-5-methylpyrrole;
1-Amino-2-(2-fluorobenzoyl)pyrrole;
1-Amino-2-benzoylpyrrole;
1-Amino-2-(2-chlorobenzoyl)pyrrole;
1-Amino-2-(2-chlorobenzoyl)-5-methylpyrrole;
1-Amino-2-(2-fluorobenzoyl)-5-methylpyrrole;
2-Benzoyl-1-methylaminopyrrole hydrobromide;
2-(2-Chlorobenzoyl)-1-methylaminopyrrole;
2-(2-Chlorobenzoyl)-1-methylamino-5-methylpyrrole;
(2-Benzoyl-1H-pyrrol-1-yl)-methyl-carbamic acid, ethyl ester;
[2-(2-Chlorobenzoyl)-1H-pyrrol-1-yl]-methyl-carbamic acid, ethyl ester;
[2-(2-Fluorobenzoyl)-1H-pyrrol-1-yl]-methyl-carbamic acid, ethyl ester;
(2-Benzoyl-1H-pyrrol-1-yl)-carbamic acid, ethyl ester;
[2-(2-Chlorobenzoyl)-1H-pyrrol-1-yl]-carbamic acid, ethyl ester;
[2-(2-Fluorobenzoyl)-1H-pyrrol-1-yl]-carbamic acid, ethyl ester;
[2-(2-Chlorobenzoyl)-5-methyl-1H-pyrrol-1-yl]-carbamic acid, ethyl ester;
2-(2-Fluorobenzoyl)-1-phthalimidopyrrole;
2-Benzoyl-1-phthalimidopyrrole;
2-(2-Chlorobenzoyl)-1-phthalimidopyrrole;
2-(2-Chlorobenzoyl)-5-methyl-1-phthalimidopyrrole;
[2-(2-Chlorobenzoyl)-1H-pyrrol-1-yl]-2-[(dimethylamino)ethyl]carbamic acid, ethyl ester hydrobromide;
[2-(2-Chlorobenzoyl)-1H-pyrrol-1yl]-2-(dimethylamino)ethylamine hydrobromide;
(2-Benzoyl-1H-pyrrol-1-yl)-2-(dimethylamino)ethylamine hydrochloride;
1-Aminoacetamido-2-benzoylpyrrole hydrochloride;
1-Aminoacetamido-2-(2-fluorobenzoyl)pyrrole hydrobromide;
1-(Phthaloyliminoacetamido)-2-benzoylpyrrole;
1-[(Carbobenzyloxyamino)acetamido]-2-benzoylpyrrole;
2-(2-Fluorobenzoyl)-1-(4-phenylpiperazin-1-ylacetamido)pyrrole;
Di-[(2-(2-fluorobenzoyl)-5-methyl-1H-pyrrol-1-yl)-2-acetamido]amine hydrochloride; and
1-(N-Methyl-acetylaminoacetylamido)-2-(2-chlorobenzoyl)-5-methylpyrrole.

The following examples are given for illustrative purposes and are not to be considered as limiting the invention disclosed herein.

EXAMPLE 1

2-(2-Fluorobenzoyl)-1-phthalimidopyrrole

To a mixture of N-phthalimidopyrrole (10 g, 47 mmole) and fused zinc chloride (10 g, 73 mmole) in 80 ml dichloroethane was added o-fluorobenzoyl chloride (7.5 g, 47 mmole). The reaction mixture was stirred at ambient temperature for twenty hours and at 80° for one hour. Thereafter, it was cooled, poured into water and extracted with dichloromethane. The organic extract was washed with water and with saturated sodium chloride solution, and dried over magnesium sulfate. The solution was filtered and evaporated to an oil which yielded a solid upon trituration with ethanol (yield 11 g, m.p. 180°–190°). This material was purified by column chromatography (silica gel, dichloromethane) to give 3 g solid. This material was recrystallized from isopropanol to give 2.6 g (17%) crystals, m.p. 202°–203°.

ANALYSIS: Calculated for $C_{19}H_{11}FN_2O_3$: 68.26% C; 3.32% H; 8.38% N; Found: 68.53% C; 3.27% H; 8.43% N.

EXAMPLE 2

1-Amino-2-(2-fluorobenzoyl)pyrrole

To a suspension of 2-(2-fluorobenzoyl)-1-phthalimidopyrrole (12.5 g, 27 mmole) in 40 ml DMF was added 40 ml methylamine (40% solution in water). After stirring one hour at ambient temperature, the reaction mixture was diluted with water and extracted with ether. The organic extract was washed with water and with saturated NaCl solution, dried over anhydrous MgSO$_4$, filtered and evaporated to 9 g oil, half of which was purified by Kugelrohr distallation (120°–130° at 0.2 mm Hg) to give 3.5 g (93%) solid, m.p. 44°–47°.

ANALYSIS: Calculated for $C_{11}H_9FN_2O$: 64.70% C; 4.44% H; 13.72% N; Found: 64.69% C; 4.64% H; 13.53% N.

EXAMPLE 3

1-Chloroacetamido-2-(2-fluorobenzoyl)pyrrole

To a solution of 1-amino-2-(2-fluorobenzoyl)pyrrole (7 g, 34 mmole) in 100 ml dichloromethane containing 5.5 g (55 mmole) sodium bicarbonate was slowly added dropwise a solution of chloroacetyl chloride (4.2 g, 38 mmole) in 15 ml dichloromethane.

After stirring one hour at ambient temperature, the reaction mixture was stirred with water and extracted with dichloromethane. The organic phase was washed with water and saturated NaCl solution, dried over anhydrous MgSO$_4$, filtered and evaporated to yield 10 g solid. This material was recrystallized from hexanes/ether to give 6 g (63%) solid, m.p. 110°–112°.

ANALYSIS: Calculated for $C_{13}H_{10}ClFN_2O_2$: 55.63% C; 3.59% H; 9.98% N; Found: 55.59% C; 3.71% H; 9.94% N.

EXAMPLE 4

1-Bromoacetamido-2-(2-fluorobenzoyl)pyrrole

To a solution of 1-amino-2-(2-fluorobenzoyl)pyrrole (19 g, 93 mmole) in 250 ml dichloromethane containing 16 g (0.19 mole) sodium bicarbonate was slowly added dropwise a solution of bromoacetyl bromide (22 g, 0.11 mole) in 50 ml dichloromethane.

After stirring two hours at ambient temperature, the reaction mixture was evaporated, dissolved in ether, washed with water and saturated NaCl solution, dried over anhydrous MgSO$_4$, filtered and evaporated to 31 g solid. This material was recrystallized from hexanes/ether to give 25 g (83%) needles, m.p. 112°–114°.

ANALYSIS: Calculated for $C_{13}H_{10}BrFN_2O_2$: 48.02% C; 3.10% H; 8.62% N; Found: 48.02% C; 3.13% H; 8.66% N.

EXAMPLE 5

5-(2-Fluorophenyl)-1H-pyrrolo[1,2-b][1,2,5]triazepin-2(3H)-one

1-Bromoacetamido-2-(2-fluorobenzoyl)pyrrole (15 g, 46 mmole) was added to 200 ml cold saturated ammonia-methanol solution. After stirring twenty hours at ambient temperature, the mixture was evaporated, stirred with water and extracted with ethyl acetate. The organic extract was washed with water and saturated NaCl solution, dried over anhydrous MgSO$_4$, filtered and evaporated to yield an oil. This oil was purified by HPLC (silica gel, 10% ethanol/dichloromethane) and then by column chromatography (silica gel, ethyl acetate) to give 1.9 g waxy solid. This material was recrystallized from acetone to give 0.8 g (7%) solid, d 189°–190°.

ANALYSIS: Calculated for $C_{13}H_{10}FN_3O$: 64.19% C; 4.14% H; 17.28% N; Found: 64.10% C; 4.17% H; 17.44% N.

EXAMPLE 6

2-(2-Fluorobenzoyl)-1-(4-phenylpiperazin-1-ylacetamido)pyrrole

A mixture of 1-bromoacetamido-2-(2-fluorobenzoyl)pyrrole (3.5 g, 11 mmole), N-phenylpiperazine (2.2 g, 14 mmole) and sodium bicarbonate (1.8 g, 22 mmole) in 120 ml dichloromethane was stirred at 75° for two hours.

The reaction mixture was cooled, concentrated to an oil, stirred with water and extracted with ether. The organic extract was washed with water and saturated NaCl solution, dried over anhydrous MgSO$_4$, filtered and evaporated to a solid which was recrystallized twice from isopropanol to give 2.6 g (59%) solid, m.p. 124°–125°.

ANALYSIS: Calculated for $C_{23}H_{23}FN_4O_2$: 67.96% C; 5.70% H; 13.79% N; Found: 67.87% C; 5.78% H; 13.58% N.

EXAMPLE 7

2-Benzoyl-1-phthalimidopyrrole

To a mixture of 1-phthalimidopyrrole (37 g, 0.17 mole) and benzoyl chloride (24 g, 0.17 mole) in 400 ml 1,2-dichloroethane was added zinc chloride (fused, 36 g, 0.26 mole).

After stirring vigorously for four hours at 70° C., the mixture was cooled, stirred with water and extracted with dichloromethane. The organic extract was washed with saturated NaCl solution, dried over anhydrous MgSO$_4$, filtered and evaporated to 60 g waxy solid. This material was purified by HPLC (silica gel, dichloromethane) to give 38 g (69%) solid. A 3 g sample was recrystallized from isopropanol to give 2.9 g crystals, m.p. 150°–152°.

ANALYSIS: Calculated for $C_{19}H_{12}N_2O_3$: 72.14% C; 3.82% H; 8.86% N; Found: 72.45% C; 3.93% H; 8.93N.

EXAMPLE 8

1-Amino-2-benzoylpyrrole

To a suspension of 2-benzoyl-1-phthalimidopyrrole (35 g, 0.11 mole) in 350 ml ethanol was slowly added 45 ml methylamine (40% solution in water). After stirring two hours at ambient temperature, the mixture was diluted with 40 ml water and extracted with ether. The ether extract was washed with water and saturated NaCl solution, dried over anhydrous MgSO$_4$, filtered and evaporated to 28 g oil which upon trituration with hexanes gave 21 g (99%) solid, m.p. 65°–69°. 3.5 g of this material was purified by HPLC (silica gel, 4% ethyl acetate/dichloromethane) to give 2.8 g solid, which was recrystallized from hexanes to give 2.4 solid, m.p. 65°–67°.

ANALYSIS: Calculated for C$_{11}$H$_{10}$N$_2$O: 70.95% C; 5.41% H; 15.05% N; Found: 71.11% C; 5.27% H; 14.98% N.

EXAMPLE 9

1Bromoacetamido-2-benzoylpyrrole

To a stirred slurry of 1-amino-2-benzoylpyrrole (14.2 g, 59.4 mmole, 78%) and sodium bicarbonate (13 g, 158 mmol) in 200 ml of dichloromethane was added a solution of bromoacetyl bromide (18.1 g, 90 mmol) in 50 ml dichloromethane over five minutes. After stirring for two hours at room temperature the volatiles were evaporated and the residue taken up in 200 ml ether. This was washed with water and brine, dried over anhydrous MgSO$_4$, filtered, and evaporated. This material was purified by HPLC (silica gel/DCM) to give 13.08 g (71%) needles, m.p. 80°–83°.

ANALYSIS: Calculated for C$_{13}$H$_{11}$BrN$_2$O$_2$: 50.83% C; 3.61% H; 9.12% N; Found: 51.16% C; 3.61% H; 9.16% N.

EXAMPLE 10

(2-Benzoyl-1H-pyrrol-1-yl)-carbamic acid, ethyl ester

To a mixture of 1-amino-2-benzoylpyrrole (12.3 g, 66 mmol) and sodium bicarbonate (13.9 g, 165 mmol) in 250 ml of dichloromethane was added a solution of ethyl chloroformate (8.2 g, 75 mmol) in 50 ml of dichloromethane. This mixture was stirred at reflux for 5 hours and then quenched with 150 ml of ice. The dichloromethane layer was separated, washed with water, dried over anhydrous Na$_2$SO$_4$, filtered and evaporated to an oil. This oil solidified upon trituration with hexane to give 16.3 g (96%) of powder, m.p. 68°–70°.

ANALYSIS: Calculated for C$_{14}$H$_{14}$N$_2$O$_3$: 65.10% C; 5.46% H; 10.84% N; Found: 65.11% C; 5.37% H; 10.84% N.

EXAMPLE 11

2-(2-Chlorobenzoyl)-1-phthalimidopyrrole

To a vigorously stirred mixture of 1-phthalimidopyrrole (45 g, 0.212 mol) and o-chlorobenzoyl chloride (37 g, 0.212 mole) in 500 ml of 1,2-dichloroethane was added freshly pulverized, fused zinc chloride (43.3 g, 0.318 mol) in one portion. The reaction mixture was heated at gentle reflux for 4.5 hours and then quenched with 700 ml of crushed ice and 500 ml of dichloromethane. The organic layer was separated and washed with water (2×500 ml), dried over anhydrous MgSO$_4$, filtered, and evaporated to give 92 g of an oil. This oil was purified by column chromatography (silica gel/dichloromethane) to give 33.8 g (45%) of needles, m.p. 158°–160° C.

ANALYSIS: Calculated for C$_{19}$H$_{11}$ClN$_2$O$_3$: 65.05% C; 3.16% H; 7.98% N; Found: 65.32% C; 3.40% H; 7.94% N.

EXAMPLE 12

5-Phenyl-1H-pyrrolo[1,2-b][1,2,5]triazepin-2(3H)-one 220 ml of an ice cold saturated ammonia-methanol solution was added dropwise over 15 minutes to an ice cold solution of 12.9 g (42 mmol) of 1-bromoacetamido-2-benzoylpyrrole in 70 ml of methanol. The reaction mixture was stirred at room temperature for 18 hours, refluxed for 3.5 hours and evaporated under reduced pressure. The residue was purified by HPLC (silica gel/5% ethanol:dichloromethane) to give 1.65 g (17.5%) of powder, m.p. 197°–199° dec.

This material was combined with 1.15 g from an earlier reaction and recrystallized from acetone to give 2.6 g cubes, m.p. 198°–200° C. dec.

ANALYSIS: Calculated for C$_{13}$H$_{11}$N$_3$O: 69.31% C; 4.92% H; 18.65% N; Found: 69.37% C; 4.92H; 18.84% N.

EXAMPLE 13

(2-Benzoyl-1H-pyrrol-1-yl)-methyl-carbamic acid, ethyl ester (2-Benzoyl-1H-pyrrol-1-yl)-carbamic acid, ethyl ester (18.5 g, 71.6 mmol) was combined with sodium carbonate (16.0 g, 157 mmol) and methyl iodide (13.2 g, 93 mmol) in 100 ml of dimethylformamide. The resulting slurry was stirred at ambient temperature for 20 hours and then at 75° C. for 2 hours. This reaction mixture was poured into 300 ml of crushed ice and extracted with four 200 ml portions of ether. The combined extracts were washed with water, dried over MgSO$_4$, filtered and evaporated to an oil which was purified by HPLC (silica gel, 15% hexane/DCM). The resulting material was recrystallized from ether-hexane to give 18.4 g (94%) of cubes, m.p. 50°–52°.

ANALYSIS:
Calculated for C$_{15}$H$_{16}$N$_2$O$_3$: 66.15% C; 5.92%H; 10.29% N; Found: 66.28% C; 6.05% H; 10.26% N.

EXAMPLE 14

2-Benzoyl-1-methylaminopyrrole hydrobromide

To a solution containing 14.9 g (54 mmol) of (2-benzoyl-1H-pyrrol-1-yl)-methyl-carbamic acid, ethyl ester in 60 ml of 95% ethanol was added a solution containing 10.9 g (273 mmol) of sodium hydroxide in 40 ml of water and the resulting slurry was stirred under reflux for 18 hours. The ethanol was removed under reduced pressure and the residue was diluted with 100 ml of water and then extracted with three 125 ml portions of ethyl acetate. The combined extracts were washed with water, dried over anhydrous MgSO$_4$, filtered and evaporated to an oil which was distilled in a Kugelrohr apparatus at 120° (0.1 mmHg) to give 9.1 g (84%) of an oil. 1.9 g of this oil was treated with 100 ml of HBr-saturated ether and the resulting precipitate was collected on a filter. This material was recrystallized from 2-propanol to give 2.1 g of solid, m.p. 180°–182° (dec).

ANALYSIS: Calculated for C$_{12}$H$_{13}$BrN$_2$O: 51.26% C; 4.66% H; 9.96% N; Found: 51.39% C; 4.77% H; 9.91% N.

EXAMPLE 15

1-(N-Methyl-bromoacetamido)-2-benzoylpyrrole

A solution of bromoacetyl bromide (8.47 g, 42 mmol) in 30 ml of dichloromethane was added over 30 minutes to a stirred slurry containing 2-benzoyl-1-methylaminopyrrole hydrobromide (14.9 g, 54.7 mmol) and sodium bicarbonate (5.9 g, 71 mmol) in 150 ml of dichloromethane. After 22 hours at room temperature the mixture was quenched with 150 ml of crushed ice and the layers were separated. The organic layer was washed with water, dried over anhydrous MgSO$_4$, filtered and evaporated. The residual oil was flash chromatographed (silica gel, 5% hexane-ethyl acetate) to give 11.0 g (98%) of crystals, m.p. 76°–78°. A 2.2 g portion of this material was recrystallized from ether-hexane to afford 2.1 g of cubes, m.p. 76°–78°.

ANALYSIS: Calculated for C$_{14}$H$_{13}$BrN$_2$O$_2$: 52.35% C; 4.07% H; 8.72% N; Found: 52.22% C; 4.01% H; 8.65% N.

EXAMPLE 16

1-Amino-2-(2-chlorobenzoyl)pyrrole 2-(2-chlorobenzoyl)-1-phthalimidopyrrole (40 g, 0.114 mmol) was suspended in 350 ml of 95% ethanol. To this rapidly stirred slurry was added 50 ml of a 40% aqueous solution of methylamine over 10 minutes. After 2.5 hours of rapid stirring the mixture was diluted with 400 ml of water and extracted with four 200 ml portions of ether. The combined extracts were washed with water, dried over anhydrous MgSO$_4$, filtered and evaporated to an oil which solidified upon standing. Trituration of this solid with hexane and collection upon a filter yielded 23.6 g (94%) of solid, m.p. 76°–78°.

ANALYSIS: Calculated for C$_{11}$H$_9$ClN$_2$O: 59.87% C; 4.11% H; 12.69% N; Found: 59.91% C; 3.97% H; 12.74% N.

EXAMPLE 17

1-(N-Methyl-aminoacetamido)-2-benzoylpyrrole fumarate

Platinum oxide (250 mg) was added under nitrogen to a solution of N-methyl-1-azidoacetamido-2-benzoylpyrrole (8.2 g, 29 mmol) and oxalic acid (2.7 g, 30 mmol) in 200 ml of methanol, and this slurry was hydrogenated at 15 psi for 2 hours. This mixture was diluted with an additional 200 ml of methanol, filtered and evaporated. The resulting residue was treated with 100 ml of saturated sodium bicarbonate solution and extracted with three 150 ml portions of ethyl acetate. The combined extracts were dried over anhydrous MgSO$_4$, filtered, evaporated and treated with a solution of fumaric acid (3.5 g, 30 mmol) in 100 ml of methanol. Evaporation under reduced pressure left a solid which was recrystallized from MeOH-ether to give 5.2 g (48%) of powder, m.p. 168°–169°.

ANALYSIS: Calculated for C$_{14}$H$_{15}$N$_3$O$_2$.C$_4$H$_4$O$_4$: 57.90% C; 5.13% H; 11.25% N; Found: 57.59% C; 5.13% H; 11.11% N.

EXAMPLE 18

1-[(Carbobenzyloxyamino)acetamido]-2-benzoylpyrrole

N,N'-Dicyclohexylcarbodiimide (2.32 g, 11.2 mmol) was added in one portion to a stirred solution of 1-amino-2-benzoylpyrrole (2.1 g, 11.2 mmol) and carbobenzyloxyglycine (2.36 g, 11.2 mmol) in 70 ml of dichloromethane. The reaction mixture was stirred rapidly for 2.5 hours at room temperature and thereafter filtered to remove the precipitated dicyclohexylurea. Evaporation of the filtrate left 4.7 g of a semi-solid which was flash chromatographed (silica gel, 1:1 ethyl acetate-hexane) to give 3.75 g (88%) of powder, m.p. 96°–98°.

ANALYSIS: Calculated for C$_{21}$H$_{19}$N$_3$O$_4$: 66.83% C; 5.07% H; 11.13% N; Found: 66.54% C; 4.88% H; 11.34% N.

EXAMPLE 19

1-(Phthaloyliminoacetamido)-2-benzoylpyrrole

To a stirred solution containing 1-amino-2-benzoylpyrrole (2.1 g, 11.2 mmol) and N-phthaloylglycine (2.3 g, 11.2 mmol) in 70 ml of dichloromethane was added dicyclohexylcarbodiimide (2.3 g, 11.2 mmol) in one portion. The resultant slurry was stirred at ambient temperature for 3 hours and then at reflux for 3 additional hours. The cooled reaction mixture was filtered and the filtrate evaporated to give 3.2 g of a solid. This solid was flash chromatographed (silica gel, 60% hexane:ethyl acetate) to afford 3.1 g (73%) of powder, m.p. 207°–209°.

ANALYSIS: Calculated for C$_{21}$H$_{15}$N$_3$O$_4$: 67.55% C; 4.04% H; 11.25% N; Found: 67.64% C; 4.32% H; 11.46% N.

EXAMPLE 20

1-Aminoacetamido-2-benzoylpyrrole hydrochloride

To an ether solution containing 1-[(t-butoxycarbonylamino)-acetamido]-2-benzoylpyrrole (18.5 g, 53.8 mmol) was added dropwise 150 ml of 4 M anhydrous HCl saturated ether solution at −10°. The reaction mixture was stirred at ambient temperature for 1 hour. The precipitated amine salt was collected on a filter to give 14.2 g of powder. This powder was recrystallized from isopropanol to give 11.2 g (74%) of powder, m.p. 218° (dec).

ANALYSIS: Calculated for C$_{13}$H$_{13}$N$_3$O$_2$.HCl: 55.81% C; 5.04% H; 15.02% N; Found: 55.51% C; 5.11% H; 15.19% N.

EXAMPLE 21

1-[(t-Butoxycarbonylamino)acetamido]-2-(2-fluorobenzoyl)pyrrole

To a solution containing 1-amino-2-(2-fluorobenzoyl)pyrrole (25.8 g, 0.126 mol) and N-(tert-butoxycarbonyl)glycine (22.4 g, 0.128 mol) in 300 ml of dichloromethane was added dicyclohexylcarbodiimide (26.4 g, 0.128 mmol) in two portions over 3 minutes. The reaction mixture was stirred at ambient temperature for 2 hours and then filtered. The filtrate was evaporated to an oil which was purified by HPLC (silica gel, 4:3 hexane-ethyl acetate) to give 37.2 g (82%) of crystals, m.p. 114°–116°.

ANALYSIS: Calculated for C$_{18}$H$_{20}$FN$_3$O$_4$: 59.82% C; 5.57% H; 11.62% N; Found: 59.98% C; 5.85% H; 11.64% N.

EXAMPLE 22

1-Aminoacetamido-2-(2-fluorobenzoyl)pyrrole hydrobromide

A stirred suspension containing 1-[(t-butoxycarbonylamino)-acetamido]-2-(2-fluorobenzoyl)pyrrole (25.2 g, 69 mmol) in 300 ml of ether was treated with 160 ml of a 0.6 M ethereal hydrogen bromide solution. The mixture was stirred at ambient temperature for 1 hour and the resultant precipitate collected on a filter. This solid was taken up in isopropanol and evaporated to a foam, which was subsequently recrystallized from isopropanol-ether to give 20.2 g (86%) of powder, m.p. 114°–116°.

ANALYSIS: Calculated for C$_{13}$H$_{13}$BrFN$_3$O$_2$: 45.62% C; 3.82% H; 12.28% N; Found: 45.20% C; 4.14% H; 12.04% N.

EXAMPLE 23

1-Methyl-5-phenyl-1H-pyrrolo[1,2-b][1,2,5]triazepin-2(3H)-one hydrobromide

A solution prepared from 1-(N-methylaminoacetamido)-2-benzoylpyrrole fumarate (1.86 g, 7.24 mmol), 2 ml of glacial acetic acid and 110 ml of methanol was refluxed under nitrogen for 5 hours. Evaporation of the volatiles left an oil which was chromatographed (silica gel, ethyl acetate) to give 1.3 g (74%) of an oil. This oil was combined with 1.0 g from an earlier reaction. The oily material was taken up in ether and treated with an excess of ethereal HBr whereupon a precipitation occurred. The precipitate was collected upon a filter and washed with ether to give 2.7 g (65% overall) of crystals, m.p. 280° (dec).

ANALYSIS: Calculated for $C_{14}H_{14}BrN_3O$: 52.51% C; 4.40% H; 13.12% N; Found: 52.57% C; 4.55% H; 13.01% N.

EXAMPLE 24

[2-(2-Chlorobenzoyl)-1H-pyrrol-1-yl]-carbamic acid, ethyl ester

1-Amino-2-(2-chlorobenzoyl)pyrrole (32 g, 0.145 mol) was combined with sodium bicarbonate (30.2 g, 0.36 mol) in 400 ml of dichloromethane. To this rapidly stirred mixture was added ethyl chloroformate (18.6 g, 0.172 mol) over 2 minutes and the resultant slurry heated under reflux for 2.5 hours. The reaction mixture was quenched with 300 ml of $H_2O$, separated, washed with $H_2O$, dried ($MgSO_4$), filtered, and evaporated to give 51 g of an oil. This oil was purified by HPLC (silica, 10:1 DCM-ethyl acetate) to give after evaporation 32.8 g (77%) of crystals, m.p. 90°–92°.

ANALYSIS: Calculated for $C_{14}H_{13}ClN_2O_3$: 57.44% C; 4.47% H; 9.57% N; Found: 57.36% C; 4.51% H; 9.56% N.

EXAMPLE 25

[2-(2-Chlorobenzoyl)-1H-pyrrol-1-yl]-methyl-carbamic acid, ethyl ester

[2-(2-Chlorobenzoyl)-1H-pyrrol-1-yl]-carbamic acid, ethyl ester (22 g, 75.1 mmol), sodium carbonate (16.0 g, 0.112 mol) and methyl iodide (13 g, 0.122 mol) were added to 100 ml of dry DMF and the mixture stirred at ambient temperature for 78 hours. The reaction was quenched with 1 liter of $H_2O$ and extracted with five 200 ml portions of diethyl ether. The combined extracts were washed with water and brine, dried ($MgSO_4$), filtered, and evaporated to give 15 g of solid. This solid was purified by HPLC (silica gel, DCM) to give 13.1 g (57%) of crystals, m.p. 54°–56°.

ANALYSIS: Calculated for $C_{15}H_{15}ClN_2O_3$: 58.73% C; 4.93% H; 9.13% N; Found: 58.62% C; 4.92% H; 9.07% N.

EXAMPLE 26

[2-(2-Chlorobenzoyl)-1H-pyrrol-1-yl]-2-[(dimethylamino)ethyl]carbamic acid, ethyl ester hydrobromide

[2-(2-Chlorobenzoyl)-1H-pyrrol-1-yl]-carbamic acid, ethyl ester (24.8 g, 85 mmol) was dissolved in 110 ml of DMF with sodium methoxide (4.8 g, 89 mmol) and the solution heated at 100° for 30 minutes. To this solution was added the free base of dimethylaminoethyl chloride hydrochloride (12.8 g, 89 mmol) in 100 ml of toluene and the solution stirred at reflux. After 2 hours, the toluene was evaporated and the reaction mixture poured into 1.5 liters of $H_2O$. Four extractions with 200 ml portions of methylene chloride, and washing with $H_2O$ and brine left a solution which was dried ($MgSO_4$) and evaporated to give 40 g of an oil. This oil was purified by HPLC (silica, 3% EtOH/DCM) to give 30.2 g (97%) of an oil.

The hydrobromide salt was prepared from 3.4 g of this oil and recrystallized from isopropanol-ether to give 2.6 g of powder, m.p. 154°–156°.

ANALYSIS: Calculated for $C_{13}H_{22}N_3O_3$·HBr: 48.60% C; 5.21% H; 9.44% N; Found: 48.32% C; 5.17% H; 9.49% N.

EXAMPLE 27

[2-(2-Chlorobenzoyl)-1H-pyrrol-1-yl]-2-(dimethylamino)ethylamine hydrobromide

[2-(2-Chlorobenzoyl)-1H-pyrrol-1-yl]-2-[(dimethylamino)ethyl]-carbamic acid, ethyl ester (26.3 g, 0.07 mol) was dissolved in 50 ml of ethanol and 70 ml of $H_2O$ containing sodium hydroxide (8.6 g, 0.216 mol). The reaction mixture was heated at reflux for 19 hours followed by evaporation of the ethanol. The aqueous solution was extracted with four 100 ml portions of ethyl acetate, washed with water and brine, dried ($MgSO_4$), filtered, and evaporated to give 14.3 g of an oil. This oil was distilled via a Kugelrohr apparatus at 150° (0.1 mmHg) to give 13.8 g (69%) of a viscous oil. 1.9 g of this oil was treated with methanolic HBr and evaporated to a powder. This powder was recrystallized from isopropanol ether to give 2.3 g of rosettes, m.p. 150°–152°.

ANALYSIS: Calculated for $C_{15}H_{18}ClN_3O$·HBr: 48.33% C; 5.13% H; 11.27% N; Found: 48.12% C; 5.32% H; 11.15% N.

EXAMPLE 28

2-(2-Chlorobenzoyl)-1-methylaminopyrrole

[2-(2-Chlorobenzoyl)-1H-pyrrol-1-yl]-methyl-carbamic acid, ethyl ester (39.2 g, 0.127 mol) was dissolved in 100 ml of ethanol and 200 ml of $H_2O$ containing sodium hydroxide (25 g, 0.625 mol). The reaction was refluxed for 18 hours followed by evaporation of the ethanol. The aqueous solution was extracted with three 300 ml portions of ethyl acetate, dried ($MgSO_4$), filtered, and evaporated to give 28 g of an oil. This oil was distilled via Kugelrohr apparatus 125° (0.15 mmHg) to give 26.3 g of a solid. This solid was triturated with hexane to give 25.5 g (85%) of crystals, m.p. 56°–58°.

ANALYSIS: Calculated for $C_{12}H_{11}ClN_2O$: 61.40% C; 4.72% H; 11.94% N; Found: 61.43% C; 4.86% H; 11.91% N.

EXAMPLE 29

1-[N-Methyl-(t-butoxycarbonylamino)acetamido]-2-(2-chlorobenzoyl)pyrrole 2-(2-Chlorobenzoyl)-1-methylaminopyrrole (23.7 g, 0.10 mol) and tert-butoxycarbonyl glycine (19.26 g, 0.11 mol) are combined in 250 ml of dichloromethane followed by addition of dicyclohexylcarbodiimide (23.7 g, 0.115 mol) over 3 minutes. The mixture was stirred at ambient temperature for 5 hours and thereafter filtered and evaporated to give 35 g of oil. This oil was purified by HPLC (silica, 2:1 hexane-ethyl acetate) to give 28 g of solid. This material was recrystallized from ether to give 26.5 g (68%) of cubes, m.p. 131°–133°.

ANALYSIS: Calculated for $C_{19}H_{22}ClN_3O_4$: 58.23% C; 5.66% H; 10.72% N; Found: 58.25% C; 5.99% H; 10.61% N.

EXAMPLE 30

1-[(t-Butoxycarbonylamino)acetamido]-2-(2-chlorobenzoyl)pyrrole

1-Amino-2-(2-chlorobenzoyl)pyrrole (24.3 g, 0.12 mol) and t-butoxycarbonyl glycine (22.7 g, 0.13 mol) were dissolved in 300 ml of dichloromethane. Dicyclohexylcarbodiimide (26.8 g, 0.13 mol) was added over 3 minutes and the reaction mixture stirred at ambient temperature for 4 hours. The resultant slurry was filtered, and the filtrate evaporated to give 65 g of oil. This oil was purified by flash chromatography (silica, 2:1 hexane-ethyl acetate) to give 21.9 g (48%) of crystals, m.p. 156°–158°.

ANALYSIS: Calculated for $C_{18}H_2OClN_3O_4$: 57.21% C; 5.33% H; 11.12% N; Found: 57.33%; 5.58% H; 11.03% N.

EXAMPLE 31

1-(N-Methyl-aminoacetamido)-2-(2-chlorobenzoyl)pyrrole hydrobromide 1-(N-Methyl-(t-butoxycarbonylamino)acetamido]-2-(2-chlorobenzoyl)pyrrole (24 g, 61.2 mmol) was dissolved in 100 ml of ethyl acetate, and 60 ml of n-propanol solution containing 12 ml of 48% HBr was added thereto with stirring. After 1 hour at 35° the solution was evaporated and the residue triturated with ether to give 23.2 g of powder. This powder was recrystallized from isopropanol-ether to give 22 g (96%) of flocculent crystals, m.p. 193°–195°.

ANALYSIS: Calculated for $C_{14}H_{14}ClN_3O_2 \cdot HBr$: 45.12% C; 4.05% H; 11.27% N; Found: 44.75% C; 4.05% H; 11.18% N.

EXAMPLE 32

5-(2-Chlorophenyl)-1-methyl-1H-pyrrolo[1,2-b][1,2,5]triazepin-2(3H)-one

A solution containing 1-(N-methyl-aminoacetamido)-2-(2-chlorobenzoyl)pyrrole hydrobromide (12.6 g, 43.4 mmol) and glacial acetic acid (15 g, 0.25 mol) in 100 ml of isopropanol was refluxed under nitrogen for 12 hours and thereafter evaporated to an oil. This oil was flash chromatographed (silica, 4:1 ethyl acetate-hexane) to give 3.2 g (27%) of crystals, m.p. 132°–134°. This was combined with 0.5 g from an earlier run and recrystallized from acetone to give 3.5 g of crystals, m.p. 132°–133.5°.

ANALYSIS: Calculated for $C_{14}H_{12}ClN_3O$: 61.42% C; 4.42% H; 15.35% N; Found: 61.57% C; 4.43% H; 15.75% N.

EXAMPLE 33

[2-(2-Fluorobenzoyl)-1H-pyrrol-1-yl]-carbamic acid, ethyl ester

1-Amino-2-(2-fluorobenzoyl)pyrrole (41 g, 0.20 mol) and sodium bicarbonate (39 g, 0.46 mol) were combined in 400 ml of dichloromethane. To this stirred slurry was added ethyl chloroformate (24 g, 0.22 mol) over 3 minutes and the reaction mixture was refluxed for 5 hours, whereupon it was quenched with 200 ml of $H_2O$ and the organic layer separated. The organic extract was washed with $H_2O$ and brine, dried ($MgSO_4$), filtered, and evaporated to an oil which crystallized upon trituration with hexane. Filtration yielded 50.8 g (92%) of crystals, m.p. 78°–80°.

ANALYSIS: Calculated for $C_{14}H_{13}FN_2O_3$: 60.86% C; 4.74% H; 10.14% N; Found: 61.21% C; 4.82% H; 10.57% N.

EXAMPLE 34

[2-(2-Fluorobenzoyl)-1H-pyrrol-1-yl]-methyl-carbamic acid, ethyl ester

Sodium carbonate (22.4 g, 0.21 mol), methyl iodide (30 g, 0.21 mol), and [2-(2-fluorobenzoyl)-1H-pyrrol-1-yl]-carbamic acid, ethyl ester (25.4 g, 0.09 mol) were combined in 100 ml of dry DMF with stirring at ambient temperature. After 72 hours, the mixture was poured into 800 ml of $H_2O$ and extracted with three 250 ml portions of DCM. The combined extracts were washed with $H_2O$ and brine, dried ($MgSO_4$), filtered and evaporated to an oil. This oil was purified by HPLC (silica, DCM) to give 26 g (97%) of crystals, m.p. 64°–66°.

ANALYSIS: Calculated for $C_{15}H_{15}FN_2O_3$: 62.05% C; 5.20% H; 9.65% N; Found: 62.11% C; 5.19% H; 9.65% N.

EXAMPLE 35

5-(2-Chlorophenyl)-1H-pyrrolo[1,2-b][1,2,5]triazepin-2(3H)-one

A suspension of 1-aminoacetamido-2-(2-chlorobenzoyl)pyrrole hydrobromide (4.9 g, 13.0 mmol) in 100 ml of ethyl acetate was treated with triethylamine (4.9 g, 48.4 mmol), filtered, and evaporated to give 3.8 g (100%) of the free base. This oily material was taken up in 70 ml of isopropanol containing glacial acetic acid (4.6 g, 76.6 mmol) and the solution was refluxed under nitrogen for 7 hours. Evaporation of the volatiles left an oil which was flash chromatographed (silica gel, 4:1 ethyl acetate-hexane) to give 0.19 g (5.3%) of powder, m.p. 215°–217° (dec.). This material was combined with other cyclization products (total weight, 1.1 g) and recrystallized from acetone to give 0.87 g (79%) of powder, m.p. 215°–216° (dec).

ANALYSIS: Calculated for $C_{13}H_{10}ClN_3O$: 60.12% C; 3.88% H; 16.18% N; Found: 60.47% C; 4.00% H; 16.39% N.

EXAMPLE 36

1-[N-Methyl-(t-butoxycarbonylamino)acetamido]-2-(2-fluorobenzoyl)pyrrole

To a solution containing 1-[N-methyl-(t-butoxycarbonylamino)acetamido]-2-(2-fluorobenzoyl)pyrrole (28 g, 0.128 mol) and N-t-butoxycarbonyl glycine (24.5 g, 0.14 mol) in 300 ml of dichloromethane was added dicyclohexylcarbodiimide (28.8 g, 0.14 mol) over 1 minute. The reaction mixture was stirred at ambient temperature for 4 hours and thereafter cooled and filtered. The filtrate was evaporated to an oil which was purified by HPLC (silica, 2:1 hexane-ethyl acetate) to give 28.8 g of solid. This material was recrystallized from ether-petroleum ether to give 27 g (56%) of crystals, m.p. 112°–114°.

ANALYSIS: Calculated for $C_{19}H_{22}FN_3O_4$: 60.78% C; 5.90% H; 11.19% N; Found: 60.79% C; 5.69% H; 11.13% N.

EXAMPLE 37

1-(N-Methyl-aminoacetamido)-2-(2-fluorobenzoyl)pyrrole hydrobromide

A slurry prepared from 1-[N-methyl-(t-butoxycarbonylamino)acetamido]-2-(2-fluorobenzoyl)pyrrole (20 g, 53.2 mmol) and 100 ml of methanol solution containing 12 ml of 48% HBr (0.106 mol) was stirred at room temperature for 6 hours. The resultant solution was evaporated to a solid which was recrystallized from isopropanol-ether to give 18 g (95%) of powder.

ANALYSIS: Calculated for $C_{14}H_{14}FN_3O \cdot HBr$: 47.20% C; 4.24% H; 11.79% N; Found: 47.32% C; 4.33% H; 11.95% N.

EXAMPLE 38

2-(2-Chlorobenzoyl)-5-methyl-1-phthalimidopyrrole

To a suspension of 1-phthalimido-2-methylpyrrole (105 g, 0.46 mol) and o-chlorobenzoyl chloride (162.5 g, 0.93 mol) in 1.5 liters of dichloromethane at 0° was added tin(IV) chloride (243 g, 0.94 mol) over 15 minutes. The resultant mixture was warmed to room temperatue over 30 minutes and then quenched with 2 liters of $H_2O$. The organic layer was washed with $H_2O$ and brine, dried ($MgSO_4$), charcoaled and filtered. Evaporation of the volatiles left an oil which was purified by flash chromatography (silica, dichloromethane) to give 126 g of powder. This powder was recrystallized from ether-petroleum ether to give 82 g (48%) of powder, m.p. 260°–262°.

ANALYSIS: Calculated for $C_{20}H_{13}ClN_2O_3$: 65.84% C; 3.59% H; 7.68% N; Found: 65.64% C; 3.63% H; 7.59% N.

EXAMPLE 39

5-(2-Fluorophenyl)-1-methyl-1H-pyrrolo[1,2-b][1,2,5]triazepin-2(3H)-one hydrochloride The free base from 1-(N-methyl-aminoacetamido)-2-(2-fluorobenzoyl)pyrrole hydrobromide (13.7 g, 38.4 mmol) was refluxed with glacial acetic acid (13.1 g, 218 mmol) in 200 ml of isopropanol for 5 hours under a nitrogen blanket. Evaporation of the volatiles left an oil which was purified by HPLC (silica, 3:1 ethyl acetate-hexane) to give 8.4 g (85%) of an oil. This oil was treated with an excess of ethereal HCl and the residue collected and air dried. This solid was recrystallized from ethanol-ether to give 8.6 g (76% overall) of powder, m.p. 210° (dec).

ANALYSIS: Calculated for $C_{14}H_{12}FN_3O \cdot HCl$: 57.24% C; 4.45% H; 14.30% N; Found: 56.87% C; 4.62% H; 14.12% N.

EXAMPLE 40

1-Amino-2-(2-chlorobenzoyl)-5-methylpyrrole

A suspension of 2-(2-chlorobenzoyl)-5-methyl-1-phthalimidopyrrole (48 g, 0.13 mol) in 200 ml of 95% ethanol was treated with 80 ml of 40% aqueous solution of methylamine and stirred at room temperature for 6 hours. The reaction was quenched with 1.5 liter of $H_2O$ and extracted with three 400 ml portions of ether. The combined ether extracts were washed with $H_2O$, dried ($MgSO_4$), filtered, and evaporated to an oil. This oil crystallized from hexane to give 22.7 g (74%) of cubes, m.p. 84°–85°.

ANALYSIS: Calculated for $C_{12}H_{11}ClN_2O$: 61.40% C; 4.72% H; 11.93% N; Found: 61.66% C; 4.72% H; 12.08% N.

EXAMPLE 41

[2-(2-Chlorobenzoyl)-5-methyl-1H-pyrrol-1-yl]-carbamic acid, ethyl ester

To a stirred slurry containing 1-amino-2-(2-chlorobenzoyl)-5-methylpyrrole (27.1 g, 0.115 mol) and sodium bicarbonate (16.8 g, 0.20 mol) in 300 ml of dichloromethane was added ethyl chloroformate (21.7 g, 0.20 mol) over 5 minutes. The reaction mixture was stirred at room temperature overnight and thereafter quenched with 500 ml of $H_2O$. The organic layer was washed with brine, dried ($MgSO_4$), charcoaled, filtered, and evaporated to an oil. This oil crystallized in hexane, which was recrystallized from ether-hexane to give 31.9 g (90%) of powder, m.p. 82°–84°.

ANALYSIS: Calculated for $C_{15}H_{15}ClN_2O_3$: 58.73% C; 4.92% H; 9.13% N; Found: 58.69% C; 4.91% H; 9.19% N.

EXAMPLE 42

8-Chloro-5-(2-fluorophenyl)-1-methyl-1H-pyrrolo[1,2-b][1,2,5]-triazepin-2(3H)-one hydrochloride A solution containing 5-(2-fluorophenyl)-1-methyl-1H-pyrrolo[1,2-b][1,2,5]triazepin-2(3H)-one hydrochloride (3.3 g, 12.9 mmol) and N-chlorosuccinimide (1.87 g, 14 mmol) in 100 ml of dry tetrahydrofuran was refluxed under $N_2$ for 3 hours. The resultant solution was evaporated and the residual oil was taken up in 200 ml of EtOAc, washed with $H_2O$, dried ($MgSO_4$), filtered, and evaporated to an oil. This oil was purified by flash chromatography (silica, 4:7 hexane-ether) to given an oil (2.1 g). This oil was treated with ethereal HCl and the resultant solid was recrystallized from isopropanol-ether to give 2.36 g (55%) of powder, m.p. 218° dec.

ANALYSIS: Calculated for $C_{14}H_{11}ClFN_3O \cdot HCl$: 51.23% C; 3.68% H; 12.80% N; Found: 51.11% C; 4.00% H; 12.75% N.

EXAMPLE 43

2-(2-Chlorobenzoyl)-1-methylamino-5-methylpyrrole

A solution containing [2-(2-chlorobenzoyl)-1H-pyrrol-1-yl]-methyl-carbamic acid, ethyl ester (29.4 g, 91 mmol) and sodium hydroxide (11 g, 275 mmol) in 50% aqueous ethanol was heated under reflux for 16 hours. The excess ethanol was evaporated and the solution was adjusted to pH 7 with 10% HCl. The resultant slurry was extracted with three 100 ml portions of DCM, dried ($MgSO_4$), filtered, and evaporated to give 22 g of solid. This solid was charcoaled and recrystallized from ether-hexane to give 21 g (93%) of powder, m.p. 107°–108°.

ANALYSIS: Calculated for $C_{13}H_{13}ClN_2O$: 62.77% C; 5.26% H; 11.26N; Found: 62.98% C; 5.20% H; 11.06% N.

EXAMPLE 44

1-(N-Methyl-bromoacetamido)-2-(2-chlorobenzoyl)-5-methylpyrrole

A stirred slurry of 2-(2-chlorobenzoyl)-1-methylamino-5-methylpyrrole (18.7 g, 75 mmol) and sodium bicarbonate (14.2 g, 170 mmol) in 100 ml of dichloromethane was treated with a solution of bromoacetyl bromide (15.2 g, 90 mmol) in 30 ml of dichloromethane over 30 minutes and stirred at room temperature overnight. The reaction mixture was quenched with 100 ml of H$_2$O, separated, washed with H$_2$O and brine, dried (MgSO$_4$), filtered, and evaporated. The resultant oil was purified by HPLC (silica, 1:1 ethyl actate-hexane) to give an oil which crystallized from ether to give 22.7 g (82%) of needles, m.p. 108°–109°.

ANALYSIS: Calculated for C$_{15}$H$_{14}$BrClN$_2$O$_2$: 48.72% C; 3.01% H; 7.57% N; Found: 48.89% C; 3.82% H; 7.50% N.

EXAMPLE 45

1-(N-Methyl-acetylaminoacetylamido)-2-(2-chlorobenzoyl)-5-methylpyrrole

To a solution containing 1-(N-methyl-bromoacetamido)-2-(2-chlorobenzoyl)-5-methylpyrrole (20.1 g, 54.5 mmol) in 150 ml of methanol at −30° was added 250 ml of 10% w/w ammonia-methanol solution over 5 minutes. The solution was warmed to room temperature over 1 hour and then heated to relux for 4 hours. The reaction mixture was evaporated to give 10.5 g of an oil. This oil was dissolved in 200 ml of isopropyl alcohol containing glacial acetic acid (18.3 g, 0.305 mol) and refluxed under nitrogen. After 72 hours the reaction mixture was evaporated and the residue was purified by HPLC (silica, 4:1 ethyl acetate-hexane) to give 4.2 g (22%) of a white powder, m.p. 139°–141° C.

ANALYSIS: Calculated for C$_{17}$H$_{18}$ClN$_3$O$_3$: 58.70% C; 5.21% H; 12.08% N; Found: 58.52% C; 5.29% H; 11.98N.

EXAMPLE 46

1-amino-2-(2-fluorobenzoyl)-5-methylpyrrole

A rapidly stirred suspension of 2-(2-fluorobenzoyl)-5-methyl-1-phthalimidopyrrole (137 g, 0.39 mol) in 500 ml of 95% ethanol was treated with 230 ml of 40% w/w solution of methylamine and the mixture was further stirred at ambient temperature for 5 hours. The mixture was diluted with 300 ml of H$_2$O and extracted with three 400 ml portions of dichloromethane. The combined extracts were dried (MgSO$_4$), filtered, and evaporated to an oil which was purified by HPLC (silica gel, DCM) to give 71 g (83%) of an oil which solidified upon seeding. A three gram portion of this material was distilled at 120° (0.1 mmHg) to give 2.9 g of solid, m.p. 45°–48°.

ANALYSIS: Calculated for C$_{12}$H$_{11}$FN$_2$O: 66.04% C; 5.08% H; 12.83% N; Found: 66.05% C; 5.13% H; 12.78% N.

EXAMPLE 47

5-(2-Fluorophenyl)-8-methyl-1H-pyrrolo[1,2-b][1,2,5]triazepin-2(3H)-one

To an ice cold solution of 1-bromoacetamido-2-(2-fluorobenzoyl)-5-methylpyrrole (42.3 g, 0.124 mol) in 100 ml of methanol was added 200 ml of 10% w/w NH$_3$/methanol solution over 10 minutes. The volatiles were evaporated under vacuum at 30° and the residue was taken up in 300 ml of isopropanol. To this solution was added glacial acetic acid (40 g, 0.60 mol) and the mixture heated under reflux for 7 hours. Evaporation of the volatiles left an oil which was purified by flash chromatography (silica gel, 4:1 EtOAc-hexane) to give 2.9 g of an oil. This oil was further purified by HPLC (silica, 2:1 EtOAc-hexane) to give 1.1 g of solid. This solid was recrystallized from ether-acetone to give 0.81 g (2.4%) of powder, m.p. 214°–216°.

ANALYSIS: Calculated for C$_{14}$H$_{12}$FN$_3$O: 65.35% C; 4.70% H; 16.33% N; Found: 65.50% C; 4.93% H; 16.42% N.

EXAMPLE 48

1-Bromoacetamido-2-(2-fluorobenzoyl)-5-methylpyrrole

To a stirred slurry containing 1-amino-2-(2-fluorobenzoyl)-5-methylpyrrole (65 g, 0.29 mol) and sodium bicarbonate (52 g, 0.62 mol) in 500 ml of dichloromethane was added bromoacetyl bromide (76.7 g, 0.38 mol) over 30 minutes. After the initial period, the reaction exotherm subsided. The reaction mixture was stirred for 3 hours and thereafter quenched with 100 ml of H$_2$O. The organic layer was separated and washed with brine, dried (MgSO$_4$), filtered, and evaporated to a solid. This solid was purified by HPLC (silica gel, DCM) to give 74 g (73%) of powder, m.p. 109°–111°.

ANALYSIS: Calculated for C$_{14}$H$_{12}$BrFN$_2$O$_2$: 49.57% C; 3.56% H; 8.26% N; Found: 49.52% C; 3.60% H; 8.31% N.

EXAMPLE 49

Di-[(2-(2-fluorobenzoyl)-5-methyl-1H-pyrrol-1-yl)-2-acetamido]amine hydrochloride To an ice cold solution of 1-bromoacetamido-2-(2-fluorobenzoyl)-5-methylpyrrole (42.3 g, 0.124 mol) in 75 ml of methanol was added 200 ml of 10% w/w ammonia-methanol solution over 20 minutes. The mixture was warmed to room temperature and maintained at that temperature for 2 hours. Evaporation of the volatiles under reduced pressure at 35° left a semisolid which was taken up in 300 ml of isopropanol and the solution was filtered. The filtrate was treated with glacial acetic acid (40 g, 0.60 mol) and refluxed for 7 hours. Evaporation of the volatiles left an oil which was purified by flash chromatography (silica, 4:1 EtOAc-hexane) to give 5 g of an oil. This oil was taken up in ether and treated with ethereal HCl. The resultant precipitate was collected and recrystallized from ethanol to give 4.9 g (6.9%) of powder, m.p. 171°–174°.

ANALYSIS: Calculated for C$_{28}$H$_{25}$F$_2$N$_5$O$_4$.HCl: 58.99% C; 4.59% H; 12.28% N; Found: 58.46% C; 4.74% H; 12.05% N.

EXAMPLE 50

(2-Benzoyl-1H-pyrrol-1-yl)-2-(dimethylamino)ethylamine hydrochloride

A solution prepared from [2-(2-benzoyl)pyrrol-1-yl]-2-[(dimethylamino)ethyl]carbamic acid, ethyl ester (51.2 g, 0.174 mol) and sodium hydroxide (28 g, 0.70 mol) and 260 ml of 50% aqueous ethanol was refluxed for 16 hours. The excess ethanol was evaporated and the residue diluted with 200 ml of H$_2$O and extracted with three 100 ml portions of DCM. The organic phase was dried (MgSO$_4$), filtered, and evaporated to an oil. This oil was distilled in a Kugelrohr apparatus (150°, 0.1 mmHg) to give 30.3 g (67.8%) of a liquid. A 3.0 g portion of this liquid was taken up in ether and treated with ethereal HCl. The resultant precipitate was collected and recrystallized from ethanol-ether to give 2.1 of powder, m.p. 149°–151°.

ANALYSIS: Calculated for $C_{15}H_{19}N_3O \cdot HCl$: 61.32% C; 6.86% H; 14.30% N; Found: 61.23% C; 6.82% H; 14.41% N.

We claim:

1. A compound of the formula

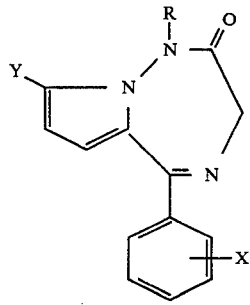

where X is hydrogen, halogen, loweralkyl, $CF_3$ or $NO_2$; Y is hydrogen, halogen or loweralkyl; and R is hydrogen, loweralkyl, loweralkylaminoloweralkyl or diloweralkylaminoloweralkyl, or a pharmaceutically acceptable acid addition salt thereof.

2. The compound as defined in claim 1, where X is hydrogen.

3. The compound as defined in claim 1, where X is halogen.

4. The compound as defined in claim 1, where R is hydrogen.

5. The compound as defined in claim 1, where R is methyl.

6. The compound as defined in claim 1, where Y is hydrogen.

7. The compound as defined in claim 1, where Y is chlorine.

8. The compound as defined in claim 1, where Y is bromine.

9. The compound as defined in claim 1, where Y is methyl.

10. The compound as defined in claim 1, where X is hydrogen and R is hydrogen.

11. The compound as defined in claim 10, where Y is hydrogen, which is 5-phenyl-1H-pyrrolo[1,2-b][1,2,5]triazepin-2(3H)-one.

12. The compound as defined in claim 1, where X is hydrogen and R is methyl.

13. The compound as defined in claim 12, where Y is hydrogen, which is 1-methyl-5-phenyl-1H-pyrrolo[1,2-b][1,2,5]triazepin-2(3H)-one.

14. The compound as defined in claim 1, where X is fluorine and R is hydrogen.

15. The compound as defined in claim 14, where Y is hydrogen.

16. The compound as defined in claim 15, where X is 2-fluoro, which is 5-(2-fluorophenyl)-1H-pyrrolo[1,2-b][1,2,5]triazepin-2(3H)-one.

17. The compound as defined in claim 14, where Y is methyl.

18. The compound as defined in claim 17, where X is 2-fluoro, which is 5-(2-fluorophenyl)-8-methyl-1H-pyrrolo[1,2-b][1,2,5]triazepin-2(3H)-one.

19. The compound as defined in claim 1, where X is fluorine and R is methyl.

20. The compound as defined in claim 19, where Y is hydrogen.

21. The compound as defined in claim 20, where X is 2-fluoro, which is 5-(2-fluorophenyl)-1-methyl-1H-pyrrolo[1,2-b][1,2,5]-triazepin-2(3H)-one.

22. The compound as defined in claim 19, where Y is chlorine.

23. The compound as defined in claim 22, where X is 2-fluoro, which is 8-chloro-5-(2-fluorophenyl)-1-methyl-1H-pyrrolo-[1,2-b] [1,2,5]triazepin-2(3H)-one.

24. The compound as defined in claim 1, where X is chlorine.

25. The compound as defined in claim 24, where R is hydrogen.

26. The compound as defined in claim 25, where Y is hydrogen.

27. The compound as defined in claim 26, where X is 2-chloro, which is 5-(2-chlorophenyl)-1H-pyrrolo[1,2-b][1,2,5]triazepin-2(3H)-one.

28. The compound as defined in claim 24, where R is methyl.

29. The compound as defined in claim 28, where Y is hydrogen.

30. The compound as defined in claim 29, where X is 2-chloro, which is 5-(2-chlorophenyl)-1-methyl-1H-pyrrolo[1,2-b][1,2,5]triazepin-2(3H)-one.

31. An analgesic composition comprising an effective pain alleviating amount of a compound of the formula

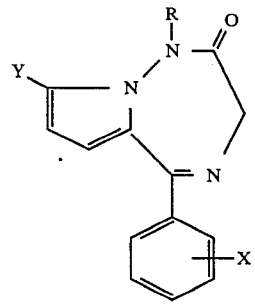

where X is hydrogen, halogen, loweralkyl, $CF_3$ or $NO_2$; Y is hydrogen, halogen or loweralkyl; and R is hydrogen, loweralkyl, loweralkylaminoloweralkyl, or diloweralkylaminoloweralkyl, or a pharmaceutically acceptable acid addition salt thereof.

32. An anxiolytic composition comprising an effective amount of anxiety alleviating amount of a compound of the formula

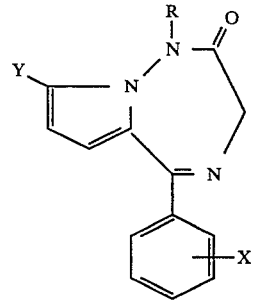

where X is hydrogen, halogen, loweralkyl, $CF_3$ or $NO_2$; Y is hydrogen, halogen or loweralkyl; and R is hydrogen, loweralkyl, loweralkylaminoloweralkyl, or diloweralkylaminoloweralkyl, or a pharmaceutically acceptable acid addition salt thereof.

* * * * *

UNITED STATES PATENT AND TRADEMARK OFFICE
CERTIFICATE OF CORRECTION

PATENT NO. : 4,517,195

DATED : May 14, 1985

INVENTOR(S) : Richard C. Effland, Joseph T. Klein R. Richard L. Hamer

It is certified that error appears in the above-identified patent and that said Letters Patent is hereby corrected as shown below:

Column 3, Line 65

"Compound IV" should be -- Compound VI --

Signed and Sealed this

Third Day of September 1985

[SEAL]

Attest:

DONALD J. QUIGG

Attesting Officer   Acting Commissioner of Patents and Trademarks - Designate

UNITED STATES PATENT AND TRADEMARK OFFICE
CERTIFICATE OF CORRECTION

PATENT NO. : 4,517,195

DATED : May 14, 1985

INVENTOR(S) : Richard C. Effland, Joseph T. Klein and R. Richard L. Hamer

It is certified that error appears in the above-identified patent and that said Letters Patent is hereby corrected as shown below:

Column 15, Line 32
"50 1" should read -- 50 µl --

Column 15, Line 35
"1nM" should read -- 1 mM --

Column 15, Line 51
"560 1" should read -- 560 µl --

Column 15, Line 52
"70 1" should read -- 70 µl --

Column 15, Line 53
"50" should read -- 50 µl --

Column 15, Line 54
"20 1" should read -- 20 µl --

Column 15, Line 56
"300 1" should read -- 300 µl --

Column 15, Line 58
"300 1" should read -- 300 µl --

Signed and Sealed this

Eleventh Day of March 1986

[SEAL]

Attest:

DONALD J. QUIGG

Attesting Officer　　　Commissioner of Patents and Trademarks